United States Patent [19]

Mikkelsen

[11] Plant 5,125

[45] Oct. 25, 1983

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 353,922

[22] Filed: Mar. 2, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Milkyway and characterized by its white flowers; variegated foliage; superior self-branching habit; tightly compact and symmetrically mounded growth habit; high floriferousness, and by its relative deterioration under low temperatures.

1 Drawing Figure

1

The present invention relates to a new and distinctive cultivar of Impatiens plant, botanically known as Impatiens, and known by the cultivar name Milkyway. The new cultivar was developed by me through controlled breeding in Ashtabula, Ohio. The seed parent was 79-1309-4 (Mikkelsen), and the pollen parent was 79-1232-4 (Mikkelsen), both of which are unpatented. Asexual reproduction of terminal or stem cuttings has shown that the unique features of this new impatiens cultivar are stabilized and are reproduced true to type in successive propagations.

The following characteristics distinguish the new impatiens from both its parent varieties and other cultivated impatients of this type known and used in the floriculture industry:

1. A distinctively white New Guinea Impatien that flowers earlier than Ringmaster, a non-patented cultivar developed by Longwood Gardens. The foliage is well variegated whereas Ringmaster is nearly solid green.

2. The new cultivar is extremely self-branching, sturdy, tightly compact, symmetrically mounded and nearly ball-shaped.

3. The flowers appear to be pure white in summer and under high light. During cool weather of autumn a very light pink tint is noticeable as petals first begin to open. The spur may be pink.

4. The flowers are somewhat more fragile outside than colored hybrids of New Guinea Impatiens, but being highly floriferous the cultivar is soon back into blossom after severe weather.

5. The cultivar has potential use in hanging baskets, pot plant use, mass plantings, and specimen plants in the garden. A combination planting of Milkyway and Solared is most eye appealing. Solared is an impatiens cultivar of the present inventor having orange-red flowers, and is disclosed in a pending application.

6. In comparison to other Mikkelsen hybrid New Guinea Impatients, the plant and flowers of Milkyway tend to deteriorate earlier under low temperatures in Ohio; plants did not survive beyond mid-October after low temperature of 2° C.

7. Mid-rib variegation develops red spotting with cool wet weather.

The accompanying colored photograph taken in mid-August in full sun outside illustrates the overall appearance of Milkyway, with the photo being a generally top perspective view of the plant and showing the colors as

2 true as it is reasonably possible to obtain in a colored reproduction of this type.

The following is a detailed description of my new impatiens cultivar based on plants produced under commercial practices in Ashtabula, Ohio. The illustrated specimen was planted outside during the second week of June from a 4" pot. By mid-August the single plant measured 50 cm. in diameter and 24 cm. high. Color references are made to The Royal Horticultural Society Colour Chart except where general terms of ordinary dictionary significance are used.

Parentage: Mikkelsen seedling 79-1309-4 crossed with Mikkelsen seedling 79-1232-4.

Propagation:

(A) *Stem cuttings.*—15 mm. long will develop to 3–4 cm. in 21–25 days.

(B) *Time to initiate root.*—8–10 days at 23° C. summer.

*Time to initiate root.*—12–14 days at 20° C. winter.

(C) *Rooting habit.*—Very fibrous, dendritic, abundant.

Plant description:

(A) *Form.*—Symmetrically rounded plant with light red to pink stems; compact, close internoded, self-branching flowering herb.

(B) *Habit of growth.*—Pink stemmed, self-branching, tightly compact medium growth rate, well textured round, mounded.

(C) *Foliage description.*—Dark green variegated, opposite on vegetative shoots, then occurring in whorls of 5–7 leaves when flowering initiates. (1) Size: 7–8 cm. long by 2–2.5 cm. wide. (2) Shape: Lanceolate, apex acuminate, base acute, young leaves slightly concave, mature leaves reflexing downward at apex. (3) Texture: Topside rugose, underside glabrous. (4) Margin: Nearly entire, slightly ciliate. (5) Color: Young foliage, top side yellow green 147-B; under side yellow green 147-B-C. Mature foliage, top side winter yellow green 147-A, summer darker than yellow green 147-A; under side yellow green 147-B-C. Basal mid rib, yellow variegation near yellow 16B. (6) Venation: Pinnate.

Flowering description:

(A) *Flowering habits.*—Flowering occurs progressively around a whorl of 5–7 leaves, usually one bloom per leaf. Flowering is continuous with open flowers and tight buds being present at the same time.

(B) *Natural flowering season.*—Indeterminate, continuous year around.

(C) *Flower bud description.*—Ellipsoidal, flowers perfect, 4.5 cm. long, light pink spur with hollow throat originating from dominant sepal; outside of tight buds light pink to nearly colorless, whereas most other cultivars are nearly red when tight.

(D) *Flowers borne.*—Individual light pink pedicels originating from whorl of leaves, pedicels and flower petals are slightly more fragile than other Mikkelsen New Guinea impatiens hybrids during severe weather, but new flowers develop quickly so the plant is only tattered for a few days.

(E) *Quantity of flowers.*—Flowers per whorl of leaves is average but the plant appears highly floriferous because of prolific self-branching which produces many flowering apices.

(F) *Petals.*—(1) Shape: Top petal dominant and isolated, nearly square; other four overlapping, heart-shaped and symmetrical. (2) Color: Top side in winter when opening, very light tinge of pink if below 55°, but pure 155-D white under high light and higher temperature during summer; under side white, with tinge of pink at sepals. (3) Number of petals: 5. (4) Size of flowers: 4–5 cm in diameter.

(G) *Reproductive organs.*—(1) Stamens: Five (5) in number. (a) Anther shape: Hooded, color light green to white. (b) Pollen color: White. (2) Pistils (a) Stigma shape: 5, segmented column, colorless. (b) Style: Colorless. (c) Ovaries: Five (5) in number, celled, 4 mm. before fertilizing; green in color; capsule explosively dehiscent.

Disease resistance: No adverse disease or insect problems seen to date.

I claim:

1. A new and distinct cultivar of impatiens plant known by the cultivar name Milkyway, as described and illustrated, and particularly characterized as to uniqueness by its white flowers, variegated foliage, superior self-branching habit, tightly compact and symmetrically mounded growth habit, high floriferousness, and by its relative deterioration under low temperatures.

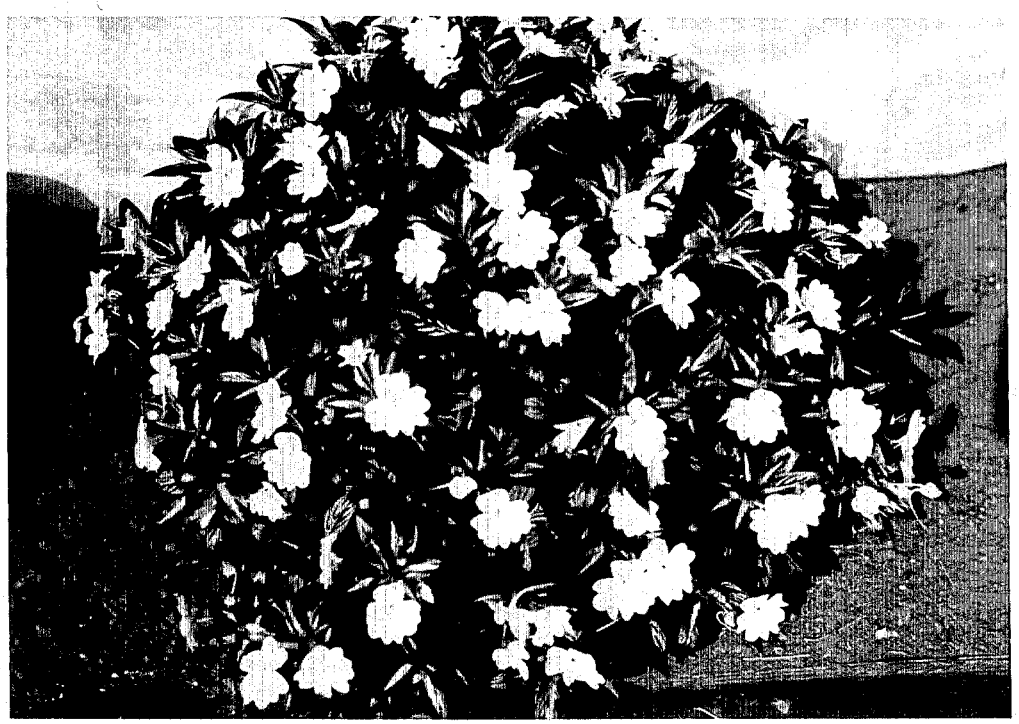

* * * * *